United States Patent
Brueckner et al.

(10) Patent No.: US 8,308,856 B2
(45) Date of Patent: Nov. 13, 2012

(54) AIR SEPARATOR, EXTERNAL FUNCTIONAL MEANS, BLOOD CIRCUIT, AND TREATMENT APPARATUS

(75) Inventors: Christoph Brueckner, Geldersheim (DE); Martin Lauer, St. Wendel (DE); Manfred Weis, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 271 days.

(21) Appl. No.: 12/765,926

(22) Filed: Apr. 23, 2010

(65) Prior Publication Data

US 2010/0269702 A1     Oct. 28, 2010

Related U.S. Application Data (60) Provisional application No. 61/185,608, filed on Jun. 10, 2009.

(30) Foreign Application Priority Data

Apr. 23, 2009  (DE) .......................... 10 2009 018 664
Jun. 10, 2009  (DE) .......................... 10 2009 024 465

(51) Int. Cl.
    *B01D 19/00*      (2006.01)
(52) U.S. Cl. ........................................... 96/211; 96/212
(58) Field of Classification Search .............. 96/212, 96/209, 210, 211
    See application file for complete search history.

(56) References Cited

U.S. PATENT DOCUMENTS

| 4,137,160 A * | 1/1979 | Ebling et al. .................... 95/259 |
| 4,345,919 A * | 8/1982 | Wilkinson et al. .............. 95/261 |
| 4,365,635 A * | 12/1982 | Bowman ....................... 600/488 |
| 4,936,759 A | 6/1990 | Clausen et al. |
| 5,211,913 A | 5/1993 | Hagiwara et al. |
| 5,258,127 A * | 11/1993 | Gsell et al. .................... 210/767 |
| 5,591,251 A * | 1/1997 | Brugger ........................ 95/242 |
| 6,066,111 A * | 5/2000 | Brockhoff .................... 604/5.01 |
| 2009/0084718 A1 * | 4/2009 | Prisco et al. .................. 210/151 |
| 2009/0084719 A1 * | 4/2009 | Childers et al. ............... 210/151 |
| 2009/0084721 A1 * | 4/2009 | Yardimci et al. .............. 210/188 |

FOREIGN PATENT DOCUMENTS

| DE | 24 20 599 A1 | 10/1975 |
| DE | 83 09 374 U1 | 12/1983 |
| DE | 196 50 407 A1 | 6/1998 |
| DE | 10 2009 012632.5 A1 | 9/2010 |
| DE | 10 2009 018664.6 A1 | 10/2010 |
| DE | 10 2009 024468.9 A1 | 12/2010 |
| EP | 0 323 341 A2 | 7/1989 |

OTHER PUBLICATIONS

International Search Report from PCT/EP2010/002486 mailed on Oct. 6, 2010.

* cited by examiner

*Primary Examiner* — Duane Smith
*Assistant Examiner* — Douglas Theisen
(74) *Attorney, Agent, or Firm* — Kenyon & Kenyon LLP (57) ABSTRACT

The present invention relates to an air separator for an extracorporeal blood circuit for separating out air from a fluid flowing through the air separator, comprising an air separation chamber having at least one inflow passage and at least one outflow passage. It further relates to an external functional apparatus, a blood circuit, and a treatment apparatus.

29 Claims, 6 Drawing Sheets

AIR SEPARATOR, EXTERNAL FUNCTIONAL MEANS, BLOOD CIRCUIT, AND TREATMENT APPARATUS

CROSS REFERENCE TO RELATED APPLICATIONS

This application claims the benefit of U.S. Provisional Application No. 61/185,608 filed Jun. 10, 2009, and claims priority to German Patent Application No. 10 2009 024 465.4 filed Jun. 10, 2009 and German Patent Application No. 10 2009018 664.6 filed Apr. 23, 2009, all of which are herein incorporated by reference in their entirety.

FIELD OF INVENTION

The present invention relates to an air separator. It further relates to an external functional means, a blood circuit, as well as a treatment apparatus.

SUMMARY OF THE INVENTION

When blood is conveyed extracorporeally there is a risk of the formation of air inclusions or air bubbles. Generally, it may be reasonable or rather necessary to remove or separate the air from the blood, e.g., before the blood is returned into the patient. It is an object of the present invention to provide an air separator suited for this purpose.

In all of the following explanations, the usage of the expression "may be or comprise" should be understood to be synonymous with "is or preferably comprises."

The air separator in accordance with the invention is suited for separating out air from a fluid flowing through the air separator and comprises at least one air separation chamber for this purpose. The air separator or the air separation chamber may be a venous blood chamber.

The expression "air separation chamber" as presently used designates a chamber or a space having a chamber interior which is suited both for receiving fluids and also for separating out gaseous components thereof. The reception may be a temporary one.

The expression "air" in the context of the present invention generally denotes "gas." The air separation chamber may therefore also be understood to be a gas separation chamber.

The expression "fluid" should preferably be understood as "liquid" or mixtures of liquids, without being restricted thereto. In accordance with the invention, other fluids may also be covered by this expression. The fluid may include gaseous constituents, in particular constituents that need to be separated out in the air separator.

In general, but without being restricted thereto, a fluid encompasses liquids such as medical liquids, e.g., blood, gases such as air, emulsions, suspensions, dispersions and the like, as well as mixtures thereof.

In accordance with the invention, the air separation chamber comprises at least one inflow passage through which the fluid or the fluid flow may flow into the air separation chamber, and at least one outflow passage through which the fluid or the fluid flow may flow out of the air separation chamber.

The expression "inflow passage" as presently used designates a passage, a conduit, or the like. The inflow passage may comprise a closed or partly closed cross-section or both. It may be a closed or partly open structure or both. The same is true for the outflow passage.

In a preferred embodiment of the present invention, the air separation chamber is subdivided into at least one first chamber having a first chamber cross-section into which the inflow passage opens, and at least one second chamber having a second chamber cross-section from which the outflow passage exits, or comprises such first and second chambers.

The expression "chamber cross-section" as presently used designates in particular a cross-section—i.e., a dimension of the circumference—of the first chamber or of the second chamber in the lengthwise direction of the respective chamber. The circumference may be round or not round. It may be closed or open.

The "lengthwise direction" of a chamber may preferably denote a horizontal extension during use of the air separator or of a treatment apparatus equipped with an air separator in accordance with the invention.

The chamber cross-section may, however, also denote a cross-section of the first chamber or of the second chamber along a widthwise direction of the respective chamber.

The chamber cross-section may be a randomly selected cross-section of the chamber. It may, but need not necessarily be the maximum chamber cross-section of the respective chamber. It may equally be the minimum chamber cross-section. The chamber cross-section may be the cross-section at a particular position of the respective first chamber or second chamber; for example, a cross-section plotted through a center point or point of gravity of the respective chamber. The chamber cross-section may furthermore be determined in a horizontal plane, in particular in a position of use of the air separator. The chamber cross-section may be determined in a plane in parallel with an opening surface or main extension surface of the connection opening.

At least one connection opening through which the fluid may flow from the first chamber into the second chamber is preferably provided between the first chamber and the second chamber. The chamber cross-section may be perpendicular to a main direction of flow of the fluid upon passing through the connection opening.

The expression "connection opening" as presently used designates an opening or a connecting passage, or passageway, for the fluid.

The air separation chamber may be subdivided into the first chamber and the second chamber by the connection opening.

The connection opening may have a diminishing cross-section. The connection opening (restriction) substantially causes a decoupling of the rotational flow in the upper (first) chamber from the substantially non-rotational flow in the lower (second) chamber.

The first chamber and the second chamber are in unidirectional or bidirectional fluid communication. Accordingly, the fluid or the fluid flow or a part or partial flow thereof may flow from the second chamber into, or back into, the first chamber, if required.

The separation of air may take place in the first chamber and/or in the second chamber of the air separation chamber.

For instance, the air may be separated out on an upper side of the first chamber. The air may additionally or alternatively be separated out in the second chamber such as, for example, on an upper side or in an upper region or in a flow niche of the second chamber.

The expression "upper side" as presently used, just like any further designations of direction or arrangement or position of components of the air separator in accordance with the invention, for instance a "lower side", in a generally preferred manner relate to the position or arrangement of the air separator in accordance with the invention during its use such as, for example, its use in a treatment apparatus.

During or for its use, the air separator is preferably arranged such that the fluid flows vertically—preferably relative to the main extension of the air separation chamber—into the air separator (not necessarily also into a chamber thereof).

The invention is, however, not limited to this; as an alternative, the air separator may be arranged horizontally during its use.

The expressions "vertical" and "horizontal" as used herein and in the claims preferably refer to the center of the Earth.

During use, the air separator may alternatively be arranged at an arbitrary angle or at an arbitrary slant relative to a vertical or horizontal line. The arrangement of the air separator during its use frequently does not, or not entirely, correspond to the arrangement or orientation of the air separator that is illustrated in the appended drawings. For the sake of simplicity, the directional expressions ("vertical" and/or "horizontal") shall in the following relate to the arrangement of the air separator that is represented in the drawing. Possible deviations resulting from an inclination of the air separator during its use are to be considered correspondingly for an understanding of the expression "vertically to the center of the Earth." The same applies for the formulations chosen in the claims.

In a preferred embodiment of the present invention, the first chamber is arranged above the second chamber during use of the air separator. Such an arrangement is shown, for instance, in FIG. 1.

The first chamber—or the space confined by it—may here be situated entirely above the second chamber or above the space confined by it, respectively. The invention does, however, also encompass the larger proportion of the first chamber to be situated above the larger proportion of the second chamber. It furthermore encompasses that the part of the first chamber opening out into the connection opening is situated above the part of the second chamber abutting against the connection opening.

In another preferred embodiment of the present invention, the air separator comprises at least one valve means which is suited for venting, or generally degassing, the air separation chamber.

A "valve means" may, for example, be a ventilation flap, an air bleed valve, a pressure valve such as a pressure relief valve, an air evacuation valve, a shut-off valve, and the like. For the purpose of better deaeration, the valve means may comprise a suction means such as, for example, a venturi nozzle.

By means of the valve means, the separated air may be conducted to an outside of the air separator. It may, for example, be discharged into the atmosphere.

The valve means may be arranged on the upper side or in an upper region of the first chamber. It may be arranged at a highest point or highest position of the air separator in accordance with the invention or of the first chamber of the air separation chamber.

Air—in particular air which was separated out at the upper side or in the upper region of the first chamber or collected there—may directly or indirectly be discharged or removed from the air separation chamber via the valve means.

Air that was separated out in the second chamber and/or is present in the second chamber after the inflow of the fluid through the connection opening from the first chamber, may be returned into the first chamber through the connection opening. It may equally be discharged from the air separation chamber through the above-mentioned valve means or another valve means which may additionally be provided, where appropriate.

In a further preferred embodiment of the present invention, the inflow passage is arranged in a lower region of the air separator or in a lower region of the first chamber.

The arrangement or position of the inflow passage or of the influx may be selected such that an inflow or influx of the fluid below the fluid level in the first chamber may advantageously also be ensured at a low or even minimum filling level of the first chamber. This may additionally contribute to deaeration or degassing of the fluid.

In another preferred embodiment of the present invention, the fluid flows tangentially into the first chamber with respect to at least one side wall of the latter.

A "side wall" or "wall" of the first chamber designates a lateral limitation of the first chamber. The first chamber preferably comprises six walls, one of which has to be understood as an upper side and another one of which has to be understood as a lower side during use of the air separator in accordance with the invention. The respective remaining walls are presently designated as "side walls."

Each one of the side walls of the first chamber may be arranged vertically during use of the air separator in accordance with the invention—independently of the orientation of the remaining side walls. It may be arranged substantially vertically or entirely vertically.

The walls of the first chamber may suitably be adapted to an inclination of the air separator in accordance with the invention, for example during its use in an external functional means. They may, for example, suitably be given a rounded configuration so that they advantageously represent a rheologically optimized area of contact for fluids flowing through the air separation chamber. The optimization may consist in achieving a suitable rotation of the fluid flowing in. The rotation may be characterized in that it promotes deaeration or degassing and/or avoids or impedes mixing of fluid and of air present inside the respective chamber.

The expression "tangential" or "tangential inflow" or "tangential influx" may designate a tangential inflow or influx of the fluid relative to a side wall of the first chamber.

The fluid may be introduced laterally through the inlet or inflow passage (the left side in FIG. 1) into the first chamber. It may subsequently spread out in a laterally tangential manner relative to the side walls of the first chamber.

A laterally tangential inflow may generate a zone with a substantially or entirely stable rotational flow of the fluid in the chamber, for example the first chamber of the air separator.

The inflow or influx of the fluid may take place at an angle from 0 degrees to 15 degrees relative to a horizontal, relative to an arrangement of the air separator as represented in the appended figures, and thus, for example, in a slightly upward orientation. It may, however, also take place in a downward orientation.

Ranges specified in the present invention should here and in the following generally be understood as inclusive ranges of values. Marginal ranges or values should therefore always be understood as being included in the respective range of values. The indicated ranges expressly also encompass any intermediary values.

In another preferred embodiment, a longitudinal section or a cross-section of the inflow passage widens in a direction towards the air separation chamber and in particular towards the first chamber.

Figure 1:
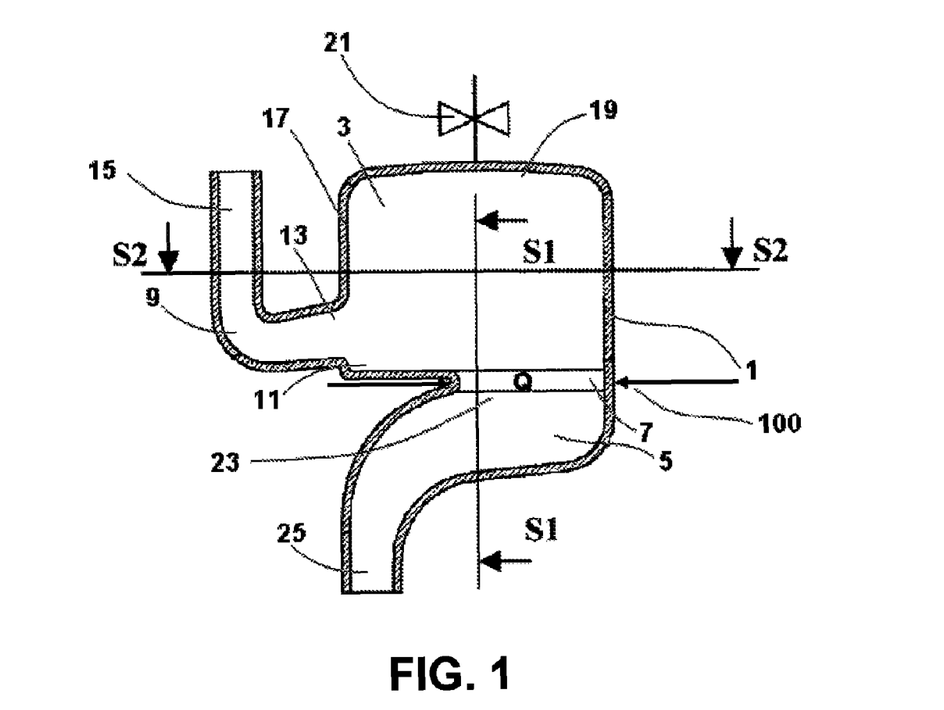
FIG. 1 shows a front view, or view from the front, of the air separator of the invention in accordance with a first embodiment.

An exemplary arrangement is shown in the appended FIG. 1.

The longitudinal section or cross-section of the inflow passage may widen continuously or continuingly. The longitudinal section or cross-section may, however, also widen in sections or steps, i.e., for example, in discrete steps.

In another preferred embodiment of the present invention, an angle of widening of the longitudinal section of the inflow passage relative to a longitudinal section of a non-widened portion of the inflow passage may be between 0 degrees and (inclusively) 15 degrees at least one longitudinal wall (e.g., top or bottom) of the inflow passage. The widening, or the widened portion of the inflow passage may have the shape of a diffuser.

In another preferred embodiment, a cross-section of flow of the connection opening or a cross-section of the connection opening where fluid passes through is smaller than the chamber cross-section of the first chamber and/or of the second chamber.

The expression "cross-section of flow" as presently used designates a cross-section of the connection opening which extends generally perpendicularly to the main direction of flow of the fluid.

In analogy with the definition of a chamber cross-section given above, the cross-section of flow of the connection opening may be a maximum cross-section or a minimum cross-section or any other cross-section of the connection opening perpendicularly to the direction of the fluid flow.

The expression "smaller" as presently used means that the cross-section of flow of the connection opening is substantially smaller than the chamber cross-section of the first chamber and/or of the second chamber, i.e., in at least one dimension (depth, width, etc.) and/or relative to a cross-sectional area. The expression "cross-section" and its composition may designate both an area or a spacing or distance, respectively.

The cross-section of flow may, for example, be half the size of a chamber cross-section.

In another preferred embodiment of the present invention, the connection opening is arranged eccentrically relative to a center axis of the first chamber and/or of the second chamber being arranged vertically during use of the air separator.

The expression "vertical center axis" here and in the following refers to an "upset" arrangement of the external functional means as represented in the appended figures. In case the external functional means is mounted in a tilted or inclined (e.g., up to 15 degrees) condition (e.g., on a treatment apparatus) this is not true any more.

Such an "exocentric" arrangement may, for example, state that center axes of the air separator and of the connection opening and/or center axes of the first chamber and of the connection opening and/or center axes of the second chamber and of the connection opening do not coincide.

An exocentric arrangement of the connection opening may also be defined such that the center axis of the connection opening is arranged offset from, for example, an axis of rotation of a rotationally symmetrical first chamber and/or second chamber and/or of a rotationally symmetrical air separator.

When the cross-section of flow of the connection opening between the first chamber and the second chamber is smaller than the chamber cross-section of the second chamber, the flow or flow rate of the fluid passing from the first chamber through the connection opening into the second chamber may slow down.

The second chamber may, for example, represent a calming zone for the fluid flow. Possibly there is substantially no rotational flow or no rotational flow at all of the fluid in such a calming zone. Such a slowed down inflow of the fluid from the first chamber through the connection opening into the second chamber may advantageously contribute to separating out air bubbles in the second chamber. For instance, air bubbles that were not separated out of the fluid or fluid flow in the first chamber may be separated out in the second chamber.

The bubbles may, for instance, gather on an upper side or in an upper region of the second chamber.

The bubbles may flow back into the first chamber through the connection opening. In case of a vertical orientation of the air separator during its use, the bubbles may ascend from the second chamber into the first chamber.

Such air having flowed back or ascended into the first chamber may gather on the upper side or in an upper region of the first chamber. It may be discharged from the air separator through the valve means.

The air separator in accordance with the invention may comprise a housing. For instance, the air separation chamber may be configured as a housing. The air separation chamber may be formed of a housing which comprises the first chamber and the second chamber.

The expression "housing" as presently used should be understood as a base body formed in particular by the upper side, the lower side, and at least two side walls of the air separation chamber. For example, the housing of the air separator may have a base body subdivided into a first chamber and a second chamber.

In a preferred embodiment of the present invention, the air separator comprises a cover means. The expression "cover means" as presently used designates a means protecting or covering an interior or inner space of the base body, i.e., of the air separation chamber or of the air separator.

The cover means may close and/or seal the interior or inner space of the air separator or of the air separation chamber against an outside. The cover means may seal the interior of the air separator in a fluid-tight manner against an outside. If required, the cover means may hermetically seal the interior of the air separator against an outside.

The expression "outside of the air separator" may be understood as to be the atmosphere. It may equally be understood to be any space outside of the air separator, for example an interior or an inner space of a treatment apparatus or of an external functional means such as a blood cassette in which the air separator in accordance with the invention is inserted.

The cover means may be provided in or on at least one portion of a side wall of the air separation chamber. The cover means may form a side wall of the air separation chamber.

The cover means may be configured as a separate component. It may be fastened to the base body. The cover means may be a lid.

A "lid" may be a non-deformable and/or relatively rigid cover means. The lid may be fastened, e.g., to one side thereof with or at the air separation chamber. By opening it or lifting it off from the side wall of the air separation chamber or from the base body of the air separation chamber, the lid may allow access to the interior of the air separation chamber.

The lid may preferably have a flat, i.e., for instance substantially planar configuration. The lid may have a curved or undulating configuration.

The cover means may be a film. Other than a lid, a "film" may, e.g., be a flexible or pliable and/or resilient cover means. The film may allow access to the interior of the air separator through the film.

In a preferred embodiment of the present invention in which a film is provided as a cover means on a side wall of the air separation chamber, the valve means may be configured for venting, for example as a phantom valve.

The expression "phantom valve" as presently used designates an element having an actor surface that may be reached by means of an actor (in the present case, for example, an actor membrane) that may assume the function of a valve.

The actor membrane is movable, extendable or curvable etc. in one direction by applying a force on it as, e.g., a pressing force. As a result of its movement or extension, the actor membrane may get into contact with an element such as a sealing means, e.g. a bar, or depart therefrom. The actor membrane may thus, for example, effect or enhance or terminate or reduce a sealing effect.

When the force acting on the actor membrane is removed, it may return, for example, to a basic position, e.g., a non-curved condition.

Such a phantom valve is described, for example, in German patent application No. 10 2009 012 632.5 filed at the German Patent and Trademark Office on Mar. 10, 2009 by the applicant of the present invention and having the title "Abdichtungseinrichtung zum Abdichten eines Volumens einer medizinischen Behandlungsanordnung gegen ein weiteres Volumen sowie Anordung and Verfahren" [Sealing means for sealing a volume of a medical treatment arrangement against another volume, as well as arrangement and method], the relevant disclosure of which is herewith fully incorporated by way of reference.

In another preferred embodiment of the present invention, the air separator may comprise at least one detection means for detecting a condition and/or a change of a condition of a chamber interior of the air separator.

The expression "detection means" as presently used designates a means that is suited for detecting and/or measuring, sensing, recording, etc. values or measurement data. Such a detection means may be a sensor, a probe, etc.

The detection of a condition and/or a change of a condition of a chamber interior of the air separator may take place, for example, by measuring at least one parameter or at least one state variable that is suited for describing the condition and/or a change of the condition of the chamber interior.

For instance, the detection means may be employed for detecting or measuring a filling level of the air separation chamber, a pressure inside the air separation chamber, a temperature inside the air separation chamber, and the like.

When the cover means is a film, detection or measurement of the condition or of a change of the condition of the chamber interior of the air separator may, for example, take place through the cover means. This may advantageously be a non-invasive measurement or detection of a condition or of the change of a condition inside the air separator in accordance with the invention.

For this purpose, the film may have a suitable film thickness, in particular a sufficiently thin film thickness.

In another preferred embodiment, the outflow passage is configured such that in case of flow cessation air present below the outflow passage may be discharged via the second or lower chamber and the first or upper chamber of the air separator.

Discharging air or air bubbles from a portion or region of the air separator from a lower region of the second chamber or from a region below the second chamber may be promoted by a suitable arrangement and/or configuration of the outflow passage.

For instance, the longitudinal section or the cross-section of the outflow passage and/or a curvature of the latter may be selected appropriately.

An example of a preferred arrangement or configuration of the outflow passage is shown in FIG. 1.

The air separator in accordance with the invention may be manufactured as a single part. It may be manufactured as a part of an external functional means, optionally designed for insertion or as an integral or one-piece component part. For instance, the air separator may be produced by means of injection molding.

The object of the invention is equally achieved through an external functional means of the invention. All the advantages of the air separator in accordance with the invention may also be obtained undiminishedly with the external functional means of the invention.

An external functional means of the invention comprises at least one air separator in accordance with the invention.

An "external functional means" may be a single-use component or a single-use article. It may be made of a plastic material.

The external functional means, or a hard part thereof, may be manufactured by means of injection molding, injection-blow molding, deep-drawing, and the like.

The external functional means of the invention may be intended for use in a treatment method. Treatment methods within the meaning of the present invention encompass medical or medical-technical treatment methods as well as treatment methods in laboratory technology.

In a preferred embodiment, the external functional means of the invention is configured as a blood cassette.

A blood cassette within the meaning of the present invention is described, for example, in application 10 2009 018 664.6 filed at the German Patent and Trademark Office on Apr. 23, 2009, or in the application 10 2009 024 468.9 filed on June 10 by the applicant of the present invention, each having the title "Externe Funktionseinrichtung, Blutbehandlungsvorrichtung zum Aufnehmen einer erfindungsgemäβen externen Funktionseinrichtung, sowie Verfahren" [External functional means, blood treatment apparatus for receiving an external functional means in accordance with the invention, and method", the respective disclosures of which are herewith fully incorporated by way of reference.

In another preferred embodiment, the external functional means is configured as an injection-molded hard part with a welded film.

The object of the invention is equally achieved through a blood circuit of the invention. All the advantages of the air separator in accordance with the invention may also be obtained undiminishedly with the blood circuit in accordance with the invention.

A blood circuit in accordance with the invention comprises at least one air separator in accordance with the invention and/or is connected to at least one external functional means in accordance with the invention.

The expression "blood circuit" as presently used may designate a tubing system for extracorporeally conducting blood.

Both the external functional means and the blood circuit may be intended for use in or on a treatment apparatus.

The object of the invention is also achieved through a treatment apparatus of the invention. All the advantages of the air separator in accordance with the invention may in turn be obtained undiminishedly with the treatment apparatus of the invention.

A treatment apparatus of the invention comprises at least one air separator in accordance with the invention and/or at least one external functional means in accordance with the invention and/or at least one blood circuit in accordance with the invention.

In a preferred embodiment of the present invention, the air separator or the external functional means may be inclined against a vertical during its use. Even at such an inclination it is advantageously possible to collect the air eliminated from the fluid in a region that is suited for venting, e.g., in the region of a valve means on an upper side of the corresponding chamber. This promotes deaeration and may contribute to a more robust operation of the air separator.

Such an "inclination angle" may be, for instance, between −15 degrees and +15 degrees, wherein the respective intermediate and marginal values are encompassed.

In a preferred embodiment of the present invention, the treatment apparatus is a blood treatment apparatus, such as a dialyzing apparatus, for performing a dialysis treatment, such as a hemodialysis, a hemofiltration, a hemodiafiltration, and the like.

The present invention is presently described as an apparatus for separating out air from blood flowing extracorporeally. The present invention is, however, expressly not intended to be limited to this. The removal of any gas from any fluid, in particular from a liquid, is equally covered by the invention as being specified here. Therefore, the use of the present invention is not limited to a medical use or to the utilization in extracorporeal blood circuits.

The present air separator is suited for separating out or removing air or other gases from a fluid flowing through the air separator. Thus it may, for example, advantageously be utilized inside an extracorporeal blood circuit in order to separate out air bubbles entrained or floating in the extracorporeally flowing blood. In this way it may advantageously be possible to avoid an infusion of air bubbles into the patient's blood circulation when returning the blood to the patient.

The air separation chamber in accordance with the invention may be provided to store a minimum quantity of the air separated out, for instance in an upper region of the first chamber. By using the valve means, the air may advantageously be removed substantially completely at any point of time, for example during filling the air separation chamber with fluid and/or from the air separation chamber already filled with fluid. In this way a smooth and/or substantially entirely air-free operation of the extracorporeal blood circuit may advantageously be ensured. The risk of infusing the air present inside an extracorporeal blood circuit into a patient when returning the blood may thus advantageously be reduced or even avoided.

The separation of air from a fluid flow may advantageously be optimized by using the air separator in accordance with the invention. This may be promoted on the one hand by the subdivision of the air separator into a first chamber—having a zone with a substantially or entirely stable rotational flow of the fluid—and a second chamber—having a calming zone for the fluid flow.

The rotational flow of the fluid in the first chamber may be obtained, for example, through a tangential inflow or influx of the fluid towards a side wall or side walls of the air separation chamber. In this way, the air may advantageously be separated out when the fluid enters into the first chamber.

Separating out air at the upper side of the first chamber may advantageously be promoted by arranging the inflow passage in a lower region of the first chamber. Thus, the air may advantageously gather already during its entry into the upper region of the first chamber and may be removed directly from the chamber through the valve means.

Separating out air on the upper side of the first chamber may be further optimized by widening the inflow passage towards the air separation chamber. Due to this widening, the inflow rate of the fluid may advantageously be reduced such that air bubbles may ascend from the entering fluid into the upper region of the chamber, to gather there.

I. a. by eccentrically arranging the connection opening between the first chamber and the second chamber, it may advantageously be achieved that a vortex core of the rotational flow of the inflowing fluid forming in the first chamber will terminate in a lower region and/or at the lower wall or lower side of the first chamber. In this way, the vortex or the eddy flow or rotational flow of the fluid in the first chamber may advantageously be stabilized, and a flow of the air bubbles from the vortex core in a downward direction, i.e., into the second chamber, may be reduced or even entirely avoided.

Due to the configuration of the cross-section of flow of the connection opening and/or configuration and/or arrangement of the outflow passage in accordance with the invention it may furthermore advantageously be possible to remove air not yet separated out during entry of the fluid, from the second chamber and/or from below the second chamber.

With the aid of the air separator in accordance with the invention, it is thus advantageously possible to achieve an efficient separation of air from the blood or fluid.

The base body of the air separator in accordance with the invention may be configured as part of an external functional means such as a blood cassette, so that even in case of inclined mounting, for example in a blood treatment apparatus, it may ensure that air will gather in an upper region of the corresponding chamber, for example of the first chamber, in particular in the region of a valve means. In this way a substantially complete removal of blood, even from an air separator arranged at an inclination during its use, may be ensured.

BRIEF DESCRIPTION OF THE DRAWINGS

In the following, the present invention shall be described by making reference to the appended drawings. In the drawings, identical reference numerals designate same or identical elements, wherein.

DETAILED DESCRIPTION OF THE DRAWINGS

FIG. 1 shows a front view of an air separator in accordance with the present invention. The air separator 100 comprises an air separation chamber 1 that is subdivided into a first chamber 3 and a second chamber 5. The air separator 100 is here exemplarily configured as a venous blood chamber.

In FIG. 1, the first chamber 3 is arranged above the second chamber 5. This arrangement may correspond to the customary use of the air separator in accordance with the invention. In such an arrangement, the first chamber 3 may therefore synonymously be designated as an upper chamber, and the second chamber 5 as a lower chamber. Between the first chamber 3 and the second chamber 5 a connection opening 7 is arranged. The connection opening 7 has a smaller cross-section of flow Q than the second chamber 5.

An inflow passage 9 is in fluid communication with the first chamber 3 and allows the inflow of a fluid into the first chamber 3. As is shown in FIG. 1, the inflow passage 9 is provided in a lower region 11 of the first chamber 3. The inflow passage 9 comprises a widening 13. A longitudinal section of the widening 13 has wider portions than a longitudinal section of the inflow passage 9 in a non-widened region 15.

During use, fluid flows through the inflow passage 9 into the first chamber 3. In the case of an arrangement exemplarily shown in FIG. 1, an inflow or influx of the fluid into the first chamber 3 takes place tangentially relative to a side wall 17, as is particularly also visible in FIGS. 3 and 4. The fluid flows in a direction towards an upper side or an upper region 19 of the first chamber 3.

Air contained in the fluid is separated out in the first chamber 3, in particular in the upper region 19 of the first chamber 3, and may be removed from the first chamber 3 through a valve means 21.

The fluid flows from the first chamber 3 through the connection opening 7 into the second chamber 5. Due to the diminishing cross-section of the connection opening 7 in comparison with a chamber cross-section of the second chamber 5—or due to the smaller cross-section, a smaller dimension, or a smaller area of the passage opening in respective comparison with the second chamber 5—the flow rate of the fluid is being reduced when fluid enters the second chamber 5.

Air not separated out yet during the inflow of the fluid into the first chamber 3 may be separated out in an upper region 23 of the second chamber 5. It may be conducted through the first chamber 3 into the upper region 19 of the first chamber 3 or ascend in order to be removed from the first chamber 3 with the aid of the valve means 21.

The second chamber 5 is connected to an outflow passage 25. The outflow passage 25 is preferably adapted such that air not separated out yet in the first chamber 3 or in the second chamber 5 is, in case of flow cessation, discharged through the outflow passage 25 into the second chamber 5 and from there through the connection opening 7 into the first chamber 3 or into an upper region 19 thereof. From there it may be removed out of the first chamber 3.

Figure 2:
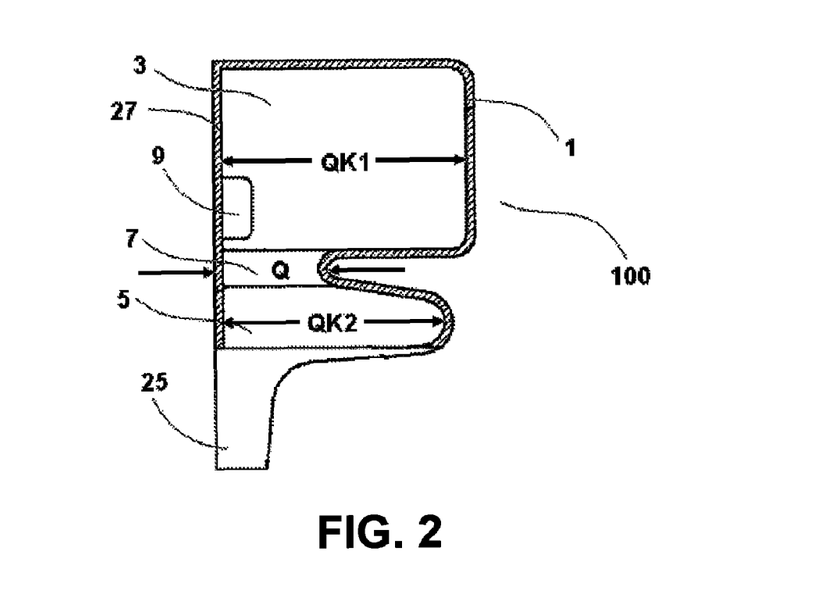
FIG. 2 shows a longitudinal sectional view of an air separator in accordance with the first embodiment.

FIG. 2 shows a lateral view of the air separator 100 in accordance with the invention in the form of a longitudinal section through the air separator of FIG. 1 along the line S1-S1 plotted in there. In the illustration of FIG. 2, it can well be seen that the connection opening 7 is arranged eccentrically between the first chamber 3 and the second chamber 5. Furthermore, it has a smaller cross-section of flow Q in comparison with a cross-section of flow QK1 of the first chamber 3. It moreover has a smaller cross-section of flow in comparison with a cross-section of flow QK2 of the second chamber. The air separator 100 comprises a cover means 27 on one side (the left side in FIG. 2).

Figure 3:
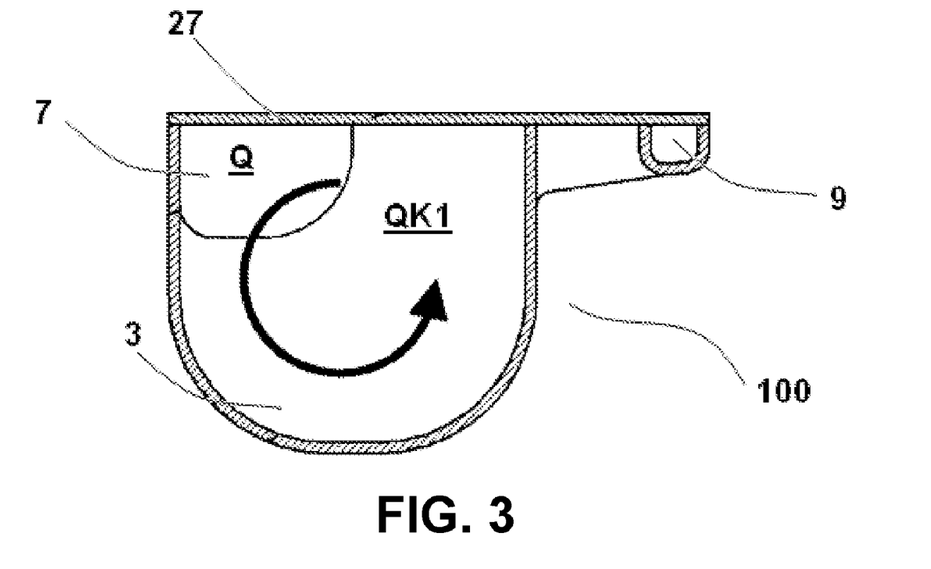
FIG. 3 shows a cross-sectional view of the air separator of FIG. 2 comprising a flat cover means.

FIG. 3 shows a cross-section of the air separator 100 in accordance with the present invention along a horizontal line of the air separator 100, denoted as line S2-S2 in FIG. 1. This cross-section shows a view onto the first chamber 3, with the observer of the illustration shown in FIG. 3 looking at the air separator 100 from above, i.e., looking at an upper side of the latter. In FIG. 3, the tangential inflow or influx of the fluid through the inflow passage 9 into the first chamber 3 is indicated by the arrow extending counter-clockwise in the form of a partial circle. The cover means 27 has a flat configuration.

Figure 4:
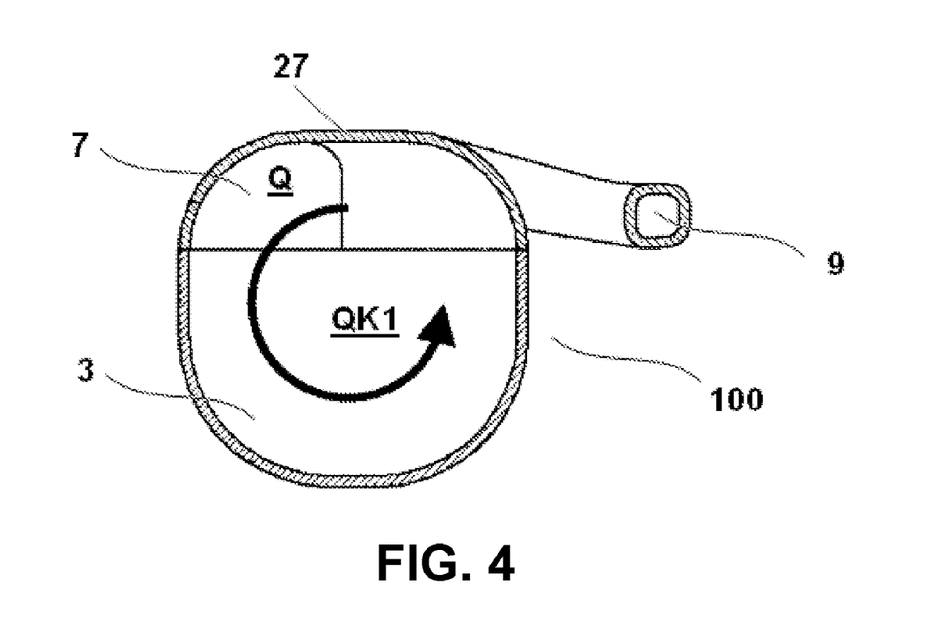
FIG. 4 shows a possible cross-section of the air separator of the invention comprising a curved cover means.

FIG. 4 equally shows a cross-section of an air separator 100 in accordance with the invention. The explanations of FIG. 3 and FIG. 4 are substantially congruous, with the exception that the cover means 27 has a curved configuration in FIG. 4.

Figure 5:
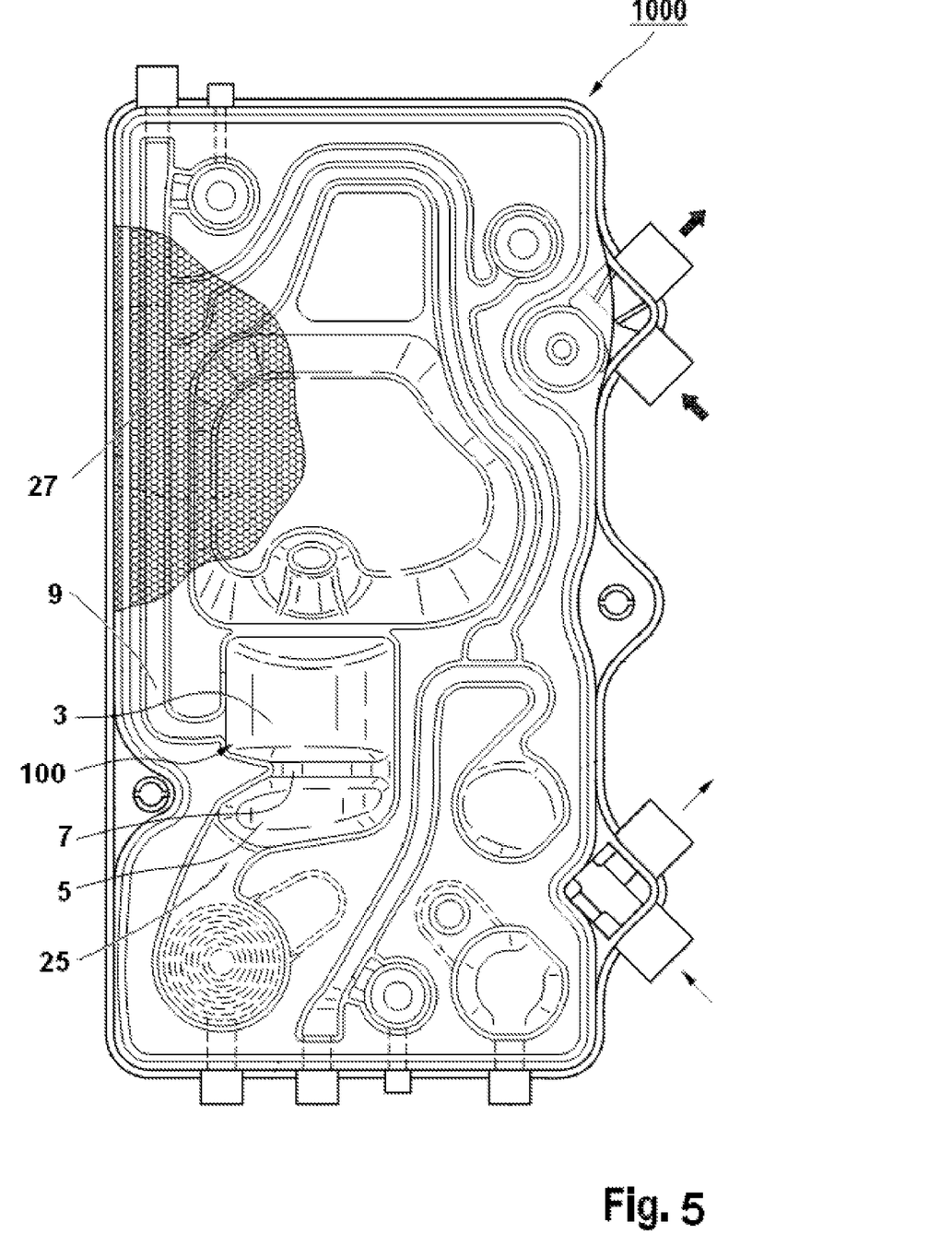
FIG. 5 shows a lateral view of a functional means of the invention in accordance with a preferred embodiment that is provided with a cover means at its front side.

FIG. 5 shows a lateral view of an external functional means in accordance with the invention, which is provided with a cover means 27 on the surface an observer of FIG. 5 looks upon.

The external functional means is here exemplarily configured as a blood treatment cassette 1000 having chambers, passages, valves, and the like. The cover means 27 covers a front side of the blood treatment cassette 1000. It is exemplarily realized as a film.

The blood treatment cassette 1000 may be coupled, at least by its front side shown in FIG. 5, to a blood treatment apparatus (not shown in FIG. 5). The blood treatment cassette 1000 comprises an air separator 100 in accordance with the invention. The air separator 100 comprises the first chamber 3 and the second chamber 5 which are separated from each other by the connection opening 7. The first chamber 3 is connected to the inflow passage 9, while the second chamber 5 is connected to the outflow passage 25.

Figure 6:
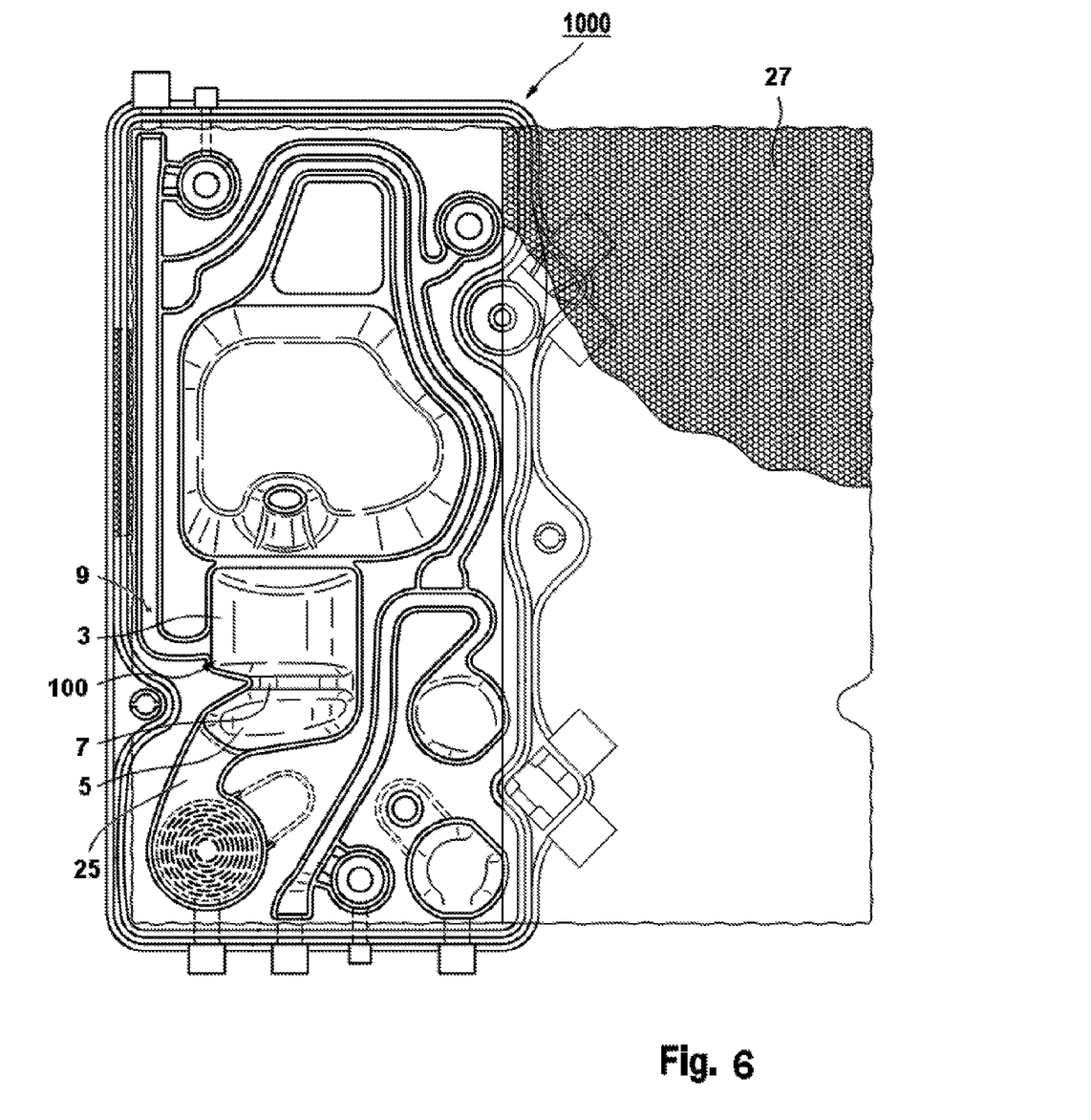
FIG. 6 shows the external functional means of FIG. 5 with a cover means which was opened after having been cut open destructively.

FIG. 6 shows the blood treatment cassette 1000 of FIG. 5, with the cover means 27 being visible at the left-hand margin of the blood treatment cassette 1000 while being cut open destructively at the top and bottom and folded open to the right.

FIG. 6 shows the elements inside the blood treatment cassette 1000 that are visible in more detail after cutting open the film. In order to avoid repetitions, reference is made to the configurations of the individual elements as discussed above in the description of FIG. 5.

Figure 7:
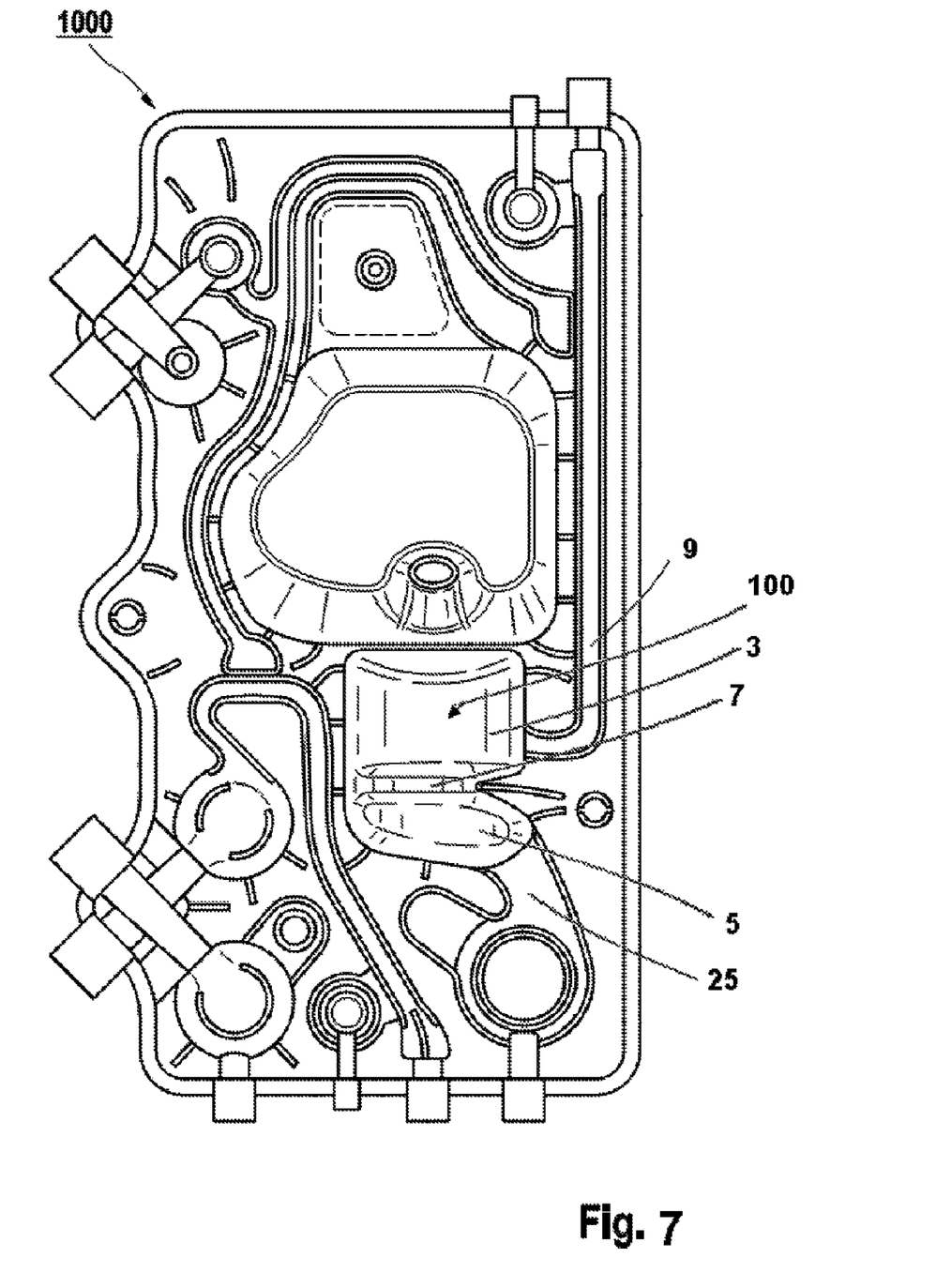
FIG. 7 shows the external functional means of FIG. 5 and FIG. 6 when viewed from its rear side.

FIG. 7 shows the blood treatment cassette 1000 from its rear side. When the blood treatment cassette 1000 is coupled to the blood treatment apparatus, an observer opening a door of the blood treatment apparatus for removing the blood treatment cassette 1000 will look upon this rear side. With regard to further details for the blood treatment cassette 1000, reference is made to its detailed description in the above-named applications directed to it, the contents of which are herewith fully incorporated into the present description.

Figure 8:
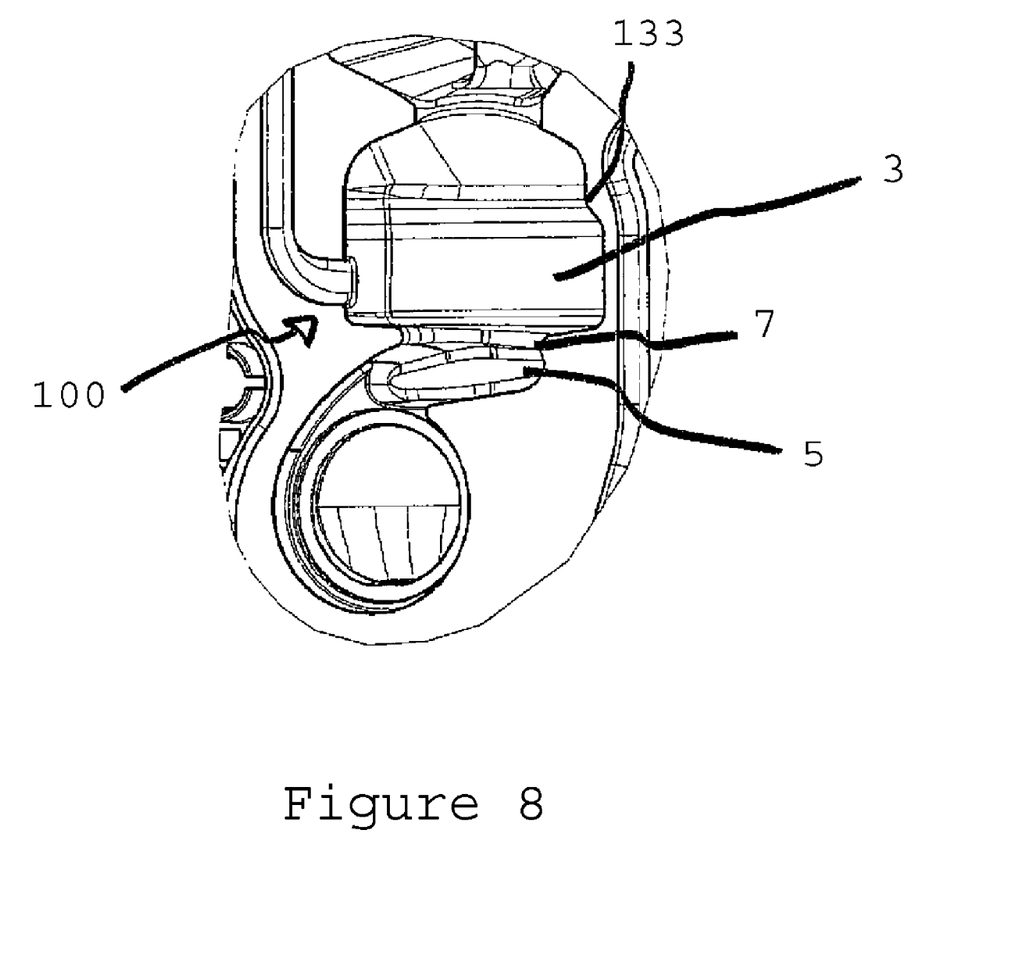
FIG. 8 shows a schematically simplified representation of a further embodiment of the air separator according to the invention.

FIG. 8 shows, in a schematically simplified representation, a further embodiment of the air separator 100 according to the invention. As can be seen from FIG. 8, the air separator 100 according to the invention comprises an indentation 133 or contraction or an inclination modification or diminution or asymmetry of the inner and/or outer wall of the air separator 100 according to the invention. In FIG. 8, the indentation 133 is shown at the right border and at the front side of the air separator 100 according to the invention.

The indentation 133 can at least be present at the side facing the supplying line. The indentation 133 can be present in a section of the periphery or at the entire periphery of the rigid part of the venous chamber. In a position of use of the blood cassette 1000, the indentation 133 can be arranged substantially horizontally. In certain embodiments, the indentation 133 can correspond to or comprise a modification of the periphery and/or of the diameter of a section of the air separator 100 according to the invention or of a wall thereof. In some embodiments, the indentation 133 can be limited to the first chamber 3. In some embodiments, with respect to a horizontal section (in relation to the representation of the blood treatment cassette 1000 in FIG. 8 or of an arrangement of the blood treatment cassette 1000 during its use), the indentation 133 can mean or can comprise a non—circular diameter of the air separator 100 according to the invention (at the level of the indentation 133).

In certain embodiments, the indentation 133 can result in an asymmetrical form of the air separator 100 according to the invention when compared with the representation of FIG. 8 in the top to bottom direction.

The indentation 133 which can partly or completely extend along the entire cross-section of the air separator according to the invention has surprisingly resulted in a reduced frothing or foam formation, respectively, within the air separator 100 according to the invention.

With the optimization of the geometry of the air separator 100 according to the invention—which can also be referred to as a venous blood chamber—achieved by means of the indentation 133 by which optionally the geometry of a single needle valve could also have been optimized, in certain embodiments of the present invention, an improved venting or priming or rinsing can be achieved prior to the beginning of the treatment. Furthermore, in some embodiments according to the invention, an improved steam flow during sterilization can be achieved. Moreover, in certain embodiments according to the invention, a reduction of eddy water spaces or areas comprising the known advantages resulting therefrom can be achieved.

LIST OF REFERENCE NUMERALS

| Reference numeral | Description |
| --- | --- |
| 100 | air separator |
| 1000 | blood treatment cassette |
| 1 | air separation chamber |
| 3 | first chamber |
| 5 | second chamber |
| 7 | connection opening |
| 9 | inflow passage |
| 11 | lower region of the upper chamber |
| 13 | widening of the inflow passage |
| 15 | non-widened region of the inflow passage |
| 17 | side wall of the first chamber |
| 19 | upper region of the first chamber |
| 21 | valve means |
| 23 | upper region of the second chamber |
| 25 | outflow passage |
| 27 | cover means |
| 133 | indentation |
| Q | cross-section of flow of the connection opening |
| QK1 | chamber cross-section of the first chamber |
| QK2 | chamber cross-section of the second chamber |

We claim:

1. An air separator for an extracorporeal blood circuit for separating out air from a fluid flowing through the air separator, comprising:
   at least one air separation chamber comprising:
      at least one inflow passage through which the fluid may flow into the air separation chamber;
      at least one outflow passage through which the fluid may flow out from the air separation chamber;
      a first chamber having at least one first chamber cross-section into which the inflow passage opens;
      a second chamber having at least one second chamber cross-section, from which the outflow passage exits; and
      a connection opening between the first chamber and the second chamber through which the fluid may flow from the first chamber into the second chamber.

2. The air separator according to claim 1, wherein the first chamber is arranged above the second chamber during use of the air separator.

3. The air separator according to claim 1, further comprising at least one valve means for venting the air separation chamber.

4. The air separator according to claim 3, wherein the at least one valve means is arranged on an upper side or in an upper region of the first chamber.

5. The air separator according to claim 1, wherein the inflow passage is arranged in a lower region of the air separator or in a lower region of the first chamber.

6. The air separator according to claim 1, wherein the inflow of the fluid takes place tangentially relative to at least one side wall of the first chamber.

7. The air separator according to claim 1, wherein the inflow of the fluid takes place at an angle of from 0 degrees to 15 degrees from horizontal.

8. The air separator according to claim 1, wherein a longitudinal section of the inflow passage widens in a direction towards the first chamber.

9. The air separator according to claim 8, wherein a cross-section of the inflow passage continuously increases in size.

10. The air separator according to claim 8, wherein an angle of widening of the longitudinal section of the inflow passage is between 0 degrees and 15 degrees.

11. The air separator according to claim 1, wherein a cross-section of flow of the connection opening is smaller than at least one of the chamber cross-section of the first chamber and the chamber cross-section of the second chamber.

12. The air separator according to claim 1, wherein the connection opening is arranged eccentrically relative to a center axis of at least one of the first chamber and the second chamber during use of the air separator.

13. The air separator according to claim 1, further comprising a cover means.

14. The air separator according to claim 13, wherein the cover means is a lid.

15. The air separator according to claim 14, wherein the lid has a flat configuration.

16. The air separator according to claim 14, wherein the lid has a curved configuration.

17. The air separator according to claim 13, wherein the cover means is a film.

18. The air separator according to claim 3, wherein the at least one valve means is a phantom valve.

19. The air separator according to claim 1, further comprising at least one detection means for detecting at least one of a condition and a change of a condition of a chamber interior of the air separator.

20. The air separator according to claim 1, wherein the outflow passage is configured such that in case of flow cessation, air present below the outflow passage may be discharged via the second chamber and the first chamber out of the air separator.

21. The air separator according to claim 1, wherein the air separator is configured to separate out air from blood.

22. An external functional means comprising:
   at least one air separator according to claim 1.

23. The external functional means according to claim 22, wherein the external functional means is a blood cassette.

24. The external functional means according to claim 22, wherein the external functional means is configured as an injection-molded hard part with at least one welded film.

25. A blood circuit comprising:
   at least one air separator according to claim 1, or
   an external functional means according to claim 22.

26. A treatment apparatus comprising:
at least one air separator according to claim 1,
at least one external functional means, and
at least one blood circuit.

27. The treatment apparatus according to claim 26, wherein at least one of the external functional means and the at least one air separator is inclined against a vertical during use of the treatment apparatus.

28. The treatment apparatus according to claim 27, wherein the inclination is between −15 degrees and +15 degrees.

29. The treatment apparatus according to claim 26, wherein the treatment apparatus is configured to treat blood.

* * * * *